(12) United States Patent
Hicks et al.

(10) Patent No.: US 6,745,061 B1
(45) Date of Patent: Jun. 1, 2004

(54) DISPOSABLE OXIMETRY SENSOR

(75) Inventors: Christopher Hicks, Boulder, CO (US); Norma M. Prince, Lyons, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/225,940

(22) Filed: Aug. 21, 2002

(51) Int. Cl.[7] .................................................. A61B 5/00
(52) U.S. Cl. ...................................... 600/344; 600/323
(58) Field of Search ................................ 600/310, 322, 600/323, 340, 344

(56) References Cited

U.S. PATENT DOCUMENTS

| | | |
|---|---|---|
| 4,825,872 A | 5/1989 | Tan et al. |
| 4,830,014 A | 5/1989 | Goodman et al. |
| 4,865,038 A | 9/1989 | Rich et al. |
| 4,964,408 A | 10/1990 | Hink et al. |
| 5,041,187 A | 8/1991 | Hink et al. |
| 5,237,994 A | 8/1993 | Goldberger |
| 5,246,003 A | 9/1993 | DeLonzor |
| 5,249,576 A | 10/1993 | Goldberger et al. |
| 5,263,244 A | 11/1993 | Centa et al. |
| 5,425,360 A | 6/1995 | Nelson |
| 5,427,093 A * | 6/1995 | Ogawa et al. ............... 600/323 |
| 5,452,717 A | 9/1995 | Branigan et al. |
| 5,469,845 A | 11/1995 | DeLonzor et al. |
| 5,520,177 A | 5/1996 | Ogawa et al. |
| 5,671,529 A | 9/1997 | Nelson ......................... 29/825 |
| 5,678,544 A | 10/1997 | DeLonzor et al. |
| 5,782,757 A * | 7/1998 | Diab et al. ................... 600/323 |
| RE36,000 E | 12/1998 | Swedlow et al. |
| 5,913,819 A | 6/1999 | Taylor et al. ................ 600/323 |
| 6,014,576 A | 1/2000 | Raley .......................... 600/344 |
| 6,073,038 A | 6/2000 | Wang et al. ................. 600/323 |

* cited by examiner

Primary Examiner—Eric F. Winakur
(74) Attorney, Agent, or Firm—Marsh Fischmann & Breyfogle LLP

(57) ABSTRACT

The invention is directed to a disposable oximetry sensor having an integrally formed connector. In one aspect, the sensor includes a clear flexible substrate on which a light emitter and/or light detector (collectively active component(s)) are mounted to allow those components to emit/detect light though the clear substrate and a second patient-side surface of that substrate. The clear substrate will generally contain one or more electrically conductive traces, preferably formed through a printing process, for interconnection to the active components. In this regard, the clear substrate acts as the electrical connector and lens structure for the active components reducing the overall part count for the sensor's assembly. Additional materials/layers may be added to the sensor including an adhesive layer, a compressible material layer, a light blocking layer, and/or a heat sink for thermal management. Generally, any additional layers/materials applied the patient-side of the clear substrate will be substantially transparent to allow light curing of adhesives utilized to connect components to the sensor though the patient-side surface of the sensor during production.

34 Claims, 13 Drawing Sheets

DISPOSABLE OXIMETRY SENSOR

FIELD OF THE INVENTION

The present invention is generally directed to photoplethysmographic measurement instruments, and more specifically to disposable pulse oximetry sensors.

BACKGROUND

A common technique used to monitor blood oxygen levels is pulse oximetry. In this regard, it is known that the light transmissivity and color of blood is a function of the oxygen saturation of the heme in the blood's hemoglobin. For example, heme that is saturated with oxygen appears bright red because saturated heme is relatively permeable to red light. In contrast, heme that is deoxygenated appears dark and bluish as it is less permeable to red light. A pulse oximeter system measures the oxygen content of arterial blood by utilizing a pulse oximetry sensor to first illuminate the blood with, for example, red and infrared radiation and determine the corresponding amounts of red and infrared radiation that are absorbed by the heme in the blood. In turn, such light absorption amounts may be employed by a pulse oximetry monitor in conjunction with known calibration information to determine blood oxygen levels.

Pulse oximetry sensors generally include one or more light emitters, a detector(s), and a means for holding these components relative to a patient's tissue. These sensors may generally be classified as reusable or disposable. Reusable sensors typically are more intricate and designed for multiple uses on multiple patients. In this regard, reusable sensors generally must be cleaned between use on different patients. Disposable sensors are typically simplified sensors that are used for a predetermined period on a single patient and discarded. Accordingly, disposable sensors may in some instances be more desirable than their reusable counterparts.

SUMMARY OF THE INVENTION

Accordingly, one object of the present invention is to provide a disposable pulse oximetry sensor that has a reduced part count and it therefore easily produced.

Another objective of the present invention is to provide a pulse oximetry sensor that lends itself to production through an automated process.

A further objective of the present invention is to provide a disposable sensor that is economical to manufacture and use while providing required sensor performance.

The inventors of the present invention have recognized the increased need for the use of disposable medical sensors and in particular disposable pulse oximetry sensors. This increased need arises due to, inter alia, concerns in properly cleaning medical instruments between uses of communicable diseases, such as AIDS and Hepatitis B. In this regard, patients as well as hospitals may prefer using new medical instruments, that is, medical instruments that have not been used previously. Additionally, the inventors have recognized that although reusable pulse oximetry sensors tend to initially be more expensive, their ability to be reused may lower their per-use cost below that of disposable pulse oximetry sensors currently existing, leaving hospitals and patients torn between their preferences and the financial realities of the health care system. Accordingly, the inventors have devised a reduced part count pulse oximetry sensor that is easily produced resulting in a disposable pulse oximetry sensor that is cost effective on a per-use basis in comparison with reusable pulse oximetry sensors.

One or more of the above objectives and additional advantages are indeed realized by the present invention where, in one aspect, a pulse oximetry sensor having an integrally formed connector is provided. The sensor includes a substantially clear flexible substrate that may be conformed about a portion of a patient's tissue, such as a finger. This flexible clear substrate may be formed from any material that provides the desired flexibility and is substantially transparent, allowing for emitting and detecting light signals through this clear substrate. A particularly apt substrate may be made from a polymer thick film (PTF) such as polyester. Mounted on a top surface of the clear flexible substrate is at least one active pulse oximetry component. That is, at least one light emitter, such as a light emitting diode, and/or a light detector, such as a photodiode. Particularly, these active components are mounted on the top surface of the clear substrate such that they emit/detect light through the clear substrate and its bottom surface. In this regard, the clear substrate acts as a lens covering the active surfaces of the light emitter and/or light detector and reducing the overall part count required for the pulse oximetry sensor. Further, as noted, the sensor has an integrally formed connector that allows the flexible substrate to be interconnected to, for example, an electrical pin connector connected to a pulse oximetry monitor.

Various refinements exist of the features noted in relation to the subject first aspect of the present invention. Further features may also be incorporated into the subject first aspect of the present invention as well. These refinements and additional features may exist individually or in any combination. For example, the bottom surface of the clear flexible substrate (i.e., the patient side of the sensor) may contain an adhesive and/or a release liner covering the adhesive for selectively securing the sensor to a patient's tissue. Additionally, a compressible material layer may be disposed on the patient side surface of the flexible sensor for increased patient comfort. Preferably, any compressible material layer utilized will contain apertures aligned with each light emitter and/or light detector mounted on the top side of the clear flexible substrate, allowing light to be emitted and/or detected through these apertures free from interference. Further, the flexible sensor may contain a light blocking layer applied to the top surface of the clear flexible substrate to minimize the effect of ambient light sources upon the sensor. This light blocking layer may include a separate substrate interconnected to the clear flexible substrate or some sort of opaque coating applied to the top surface of the clear flexible substrate.

Regardless of which additional features the sensor utilizes, in a one embodiment, all materials applied to the bottom surface (i.e., patient side) of the clear flexible substrate contain a substantially clear portion aligned with the active pulse oximetry components. As will be appreciated, this provides for increased light transfer between a light emitter and/or detector upon application to an appendage as well as allowing for the utilization of light (e.g., ultra violet (UV) light or high intensity visible light) to cure various light-curable adhesives that may be used to mount one or more of the components to the clear flexible substrate during manufacture. For example, the light emitter and/or detector may be encapsulated on top of the clear substrate using a light-curable clear adhesive to stabilize the emitter/detector as well as provide increased focusing of light into or from the clear substrate. Light may be applied through these layers and the bottom surface of the clear substrate to cure the adhesive(s). In a further embodiment, all the materials applied to the bottom surface of the clear substrate will be at least partially transparent materials to allow light curable adhesives to be utilized in laminating the various materials together. In addition, or alternatively, thermal and/or mechanical pressure may be utilized to initiate or complete the cure of adhesives as well as thermally bond (i.e., laminate) one or more of the various material layers together.

In a second aspect of the present invention, a pulse oximetry sensor is provided comprising a substantially clear flexible substrate that may be conformed about a patient's tissue having, mounted on its top surface, at least one active pulse oximetry component. Again these active components (i.e., light emitter and/or light detector) are mounted on the clear substrate's top surface such that they emit/detect light through the clear substrate and its bottom surface. Further, the sensor includes at least one electrically conductive trace formed on the clear flexible substrate. The electrically conductive trace(s) is formed on the same surface (i.e., top surface) on which the emitters/detectors are mounted and provides an electrical connection between the integrally formed connector and the active components. This trace may be formed of any appropriate conductive material so long as it allows the substrate to freely flex. Examples of appropriate materials include thin metallic foils (e.g., 0.001 in) that may be stamped onto and/or melted into the clear substrate and conductive inks that may be printed onto the clear substrate.

Light emitters and detectors typically include a semiconductor die that contains first and second electrical contact pads that must be electrically interconnected with a power source to function. In this regard the light emitter and/or detector will be electrically interconnected to at least one electronically conductive trace. That is the emitter/detector may be mounted such that it electrically contacts the conductive trace using, for example, a conductive epoxy to attach an electrical contact pad on the emitter/detector to one or more electrically conductive traces.

Various refinements exist of the features in relation to the subject second aspect of the present invention. For example, the clear flexible substrate may have a plurality of electrical conductive traces formed on the surface containing the emitter and/or detector. In this regard, the active components (i.e., emitter and detector) may each be electrically interconnected to first and second electrical traces. That is, each active component may be electrically interconnected to "out" and "return" legs of what forms an electrical circuit when the sensor is connected to a pulse oximetry monitor. Further, the subject second aspect of the present invention may utilize any additional components interconnected to the flexible substrate such as those discussed above in reference to the first aspect of the present invention. Again, any additional components interconnected to the bottom surface of the subject second aspect of the present invention will preferably be at least partially transparent to realize the above described benefits.

In one embodiment of the second aspect of the present invention, the conductive traces are formed on the clear flexible substrate using a conductive ink, such as a silver epoxy, that is deposited onto the clear substrate. In this regard, the conductive traces may be deposited on the clear flexible substrate using a printing process such as, but not limited to, inkjet printing, screen printing, or pad printing. As will be appreciated, the use of ink printing allows for formation of conductive traces on the clear flexible substrate in a simplified manner in comparison to the utilization of, for example, chemical etching of a conductive surface such as copper, the use of a stamped lead frame, and/or the use of discrete wire conductors.

In a related aspect of the present invention, a pulse oximetry sensor is provided having a clear flexible substrate with at least one electrically conductive trace formed thereon and at least one light emitter electrically interconnected to one or more of those traces. The sensor further includes a thermal element adapted to transfer thermal energy away from the light emitter. As will be appreciated, when the light emitter is active (i.e., emitting light) the light emitter and the clear substrate to which it is mounted may become uncomfortably warm. This is especially evident where conductive ink traces are utilized on the clear flexible substrate, as conductive ink traces may not have enough thermal mass to effectively transfer heat away from the light emitter. Accordingly, undue heat build up around the light emitter may result in patient discomfort and/or tissue damage. Though in the present invention the thermal element is utilized to counteract the reduced thermal mass resulting from use of printed conductive traces, it will be appreciated that a thermal element may also be utilized with any pulse oximetry sensor to reduce potentially damaging heat concentrations. The thermal element may be formed of any material having high thermal conductivity such as, but not limited to, a copper sheet or washer that is thermally connected to the light emitter. In any case, the thermal element acts as a heat sink operable to draw heat away from the light emitter and dissipate that heat over an increased area to prevent excessive heat build up in a single area adjacent to a patient's tissue.

A related aspect of the present invention provides a sensor utilizing a clear flexible substrate on which a light emitter and/or detector is mounted for emitting/detecting light through the clear flexible substrate. This sensor further incorporates an insulative layer in a face-to-face relationship with at least a portion of a patient side surface (i.e., the bottom surface of the clear substrate) for creating a temperature differential between a patient's tissue and the bottom surface of the clear flexible substrate. As noted above, sensor active components and, in particular, the light emitting components may become uncomfortably warm during normal usage. In this regard, the insulative layer may be disposed on the bottom surface of the clear flexible substrate to provide a thermal buffer or "stand-off" between a patient's tissue and the bottom surface of the clear substrate.

In one embodiment, this insulative layer will contain apertures aligned with each of the active components mounted on the top surface of the clear flexible substrate. This arrangement allows the active components to emit/detect light free from interference. In a further embodiment utilizing the insulative layer, a substantially clear interconnecting layer will be interconnected to patient side surface of the insulative layer allowing the apertures within the insulative layer to be sandwiched between the clear interconnecting layer and the patient surface of the clear substrate. As will be appreciated, this produces an air pocket of "dead" air space between the patient's tissue and the bottom surface of the clear substrate, further reducing the possibility of undue heat build up against a patient's tissue. This pocket is preferably sealed to prevent the pocket deflation when the sensor is applied to the patient's tissue. Adhesives and/or thermal bonding of the various layers may be utilized to producing a sealed pocket.

In a further related aspect of the present invention, the flexible pulse oximetry sensor utilizes a first substrate having a top surface with one or more electrically conductive traces formed thereon and a second flexible substrate having a bottom surface with one or more electrical conductive traces formed thereon. In this embodiment, one or more active sensor components (i.e. light emitters/detectors) are physically and electronically mounted to one of the substrates as well as being electrically interconnected to a conductive trace on the second flexible substrate. In this regard, the first and second flexible substrates may be disposed in a face-to-face relationship where the top and bottom surfaces containing the electrically conductive traces are disposed towards one another. As will be appreciated, this provides a sensor where the electrical traces, such as printed conductive ink traces, as well as the active sensor components are sandwiched between the first and second substrates and are thereby protected from the environment.

One or more of the above noted objectives and advantages may also be realized by an inventive method for forming a pulse oximetry sensor. The inventive method includes the steps of mounting onto the top surface of a substantially clear substrate, a light emitter for emitting light through the bottom surface of the substrate and/or a light detector for detecting light through the bottom surface of the substrate. The step of mounting may further include the step of electrically connecting the emitter/detector to one or more electrical traces associated with the clear substrate using, for example, a conductive epoxy. The mounting step may also include encapsulating the emitter/detector with a clear adhesive for increasing the light focusing capabilities of that component. The method further includes the step of applying light through the bottom surface of the clear substrate to at least partially cure one or more light-curable adhesives used for mounting emitters/detectors to the clear substrate.

A method is also provided for producing a flexible sensor having an integrally formed cord as well as an integrally formed connector. The process includes the steps of depositing at least one electrically conductive trace between first and second points on the surface of a flexible substrate sheet, which may be a clear flexible substrate. In order to produce an integrally formed cord having a length greater than that of the longest edge of the flexible substrate sheet, these traces are formed in a concentric pattern, continuously winding about a first point and gradually approaching a second point. For example, a first point may be located near the middle of a substantially square substrate sheet while the second point is located at one of the corners of the substrate sheet. The electrical traces connect the first and second points by winding about the first point in, for example, a circular or rectangular spiral pattern until they reach the second point. In one embodiment, the electrically conductive traces are formed between the first and second points on the substrate sheet using a conductive ink printing processes. Additionally, at least one light emitter and/or light detector are mounted on the flexible substrate and are electrically interconnected the conductive traces. Preferably, these emitters/detectors are mounted at the end of a trace to maximize the resulting length of the cord. Finally, the flexible substrate is cut between concentric windings of the electrical trace between the first and second points to form a flexible concentric strip having at least one electrically conductive trace between its first and second ends. This flexible concentric strip is then straightened to provide a flexible sensor having an integrally formed cord.

DETAILED DESCRIPTION

Figure 1:
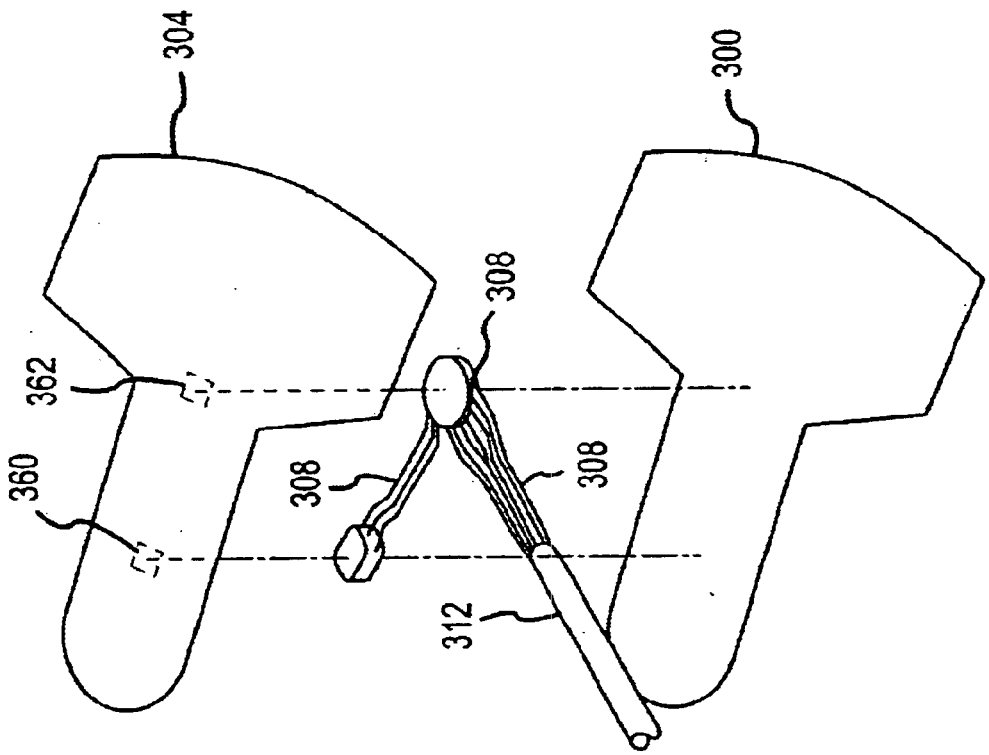
FIG. 1 shows an exploded perspective view of a prior art pulse oximetry sensor.
Figure 1:
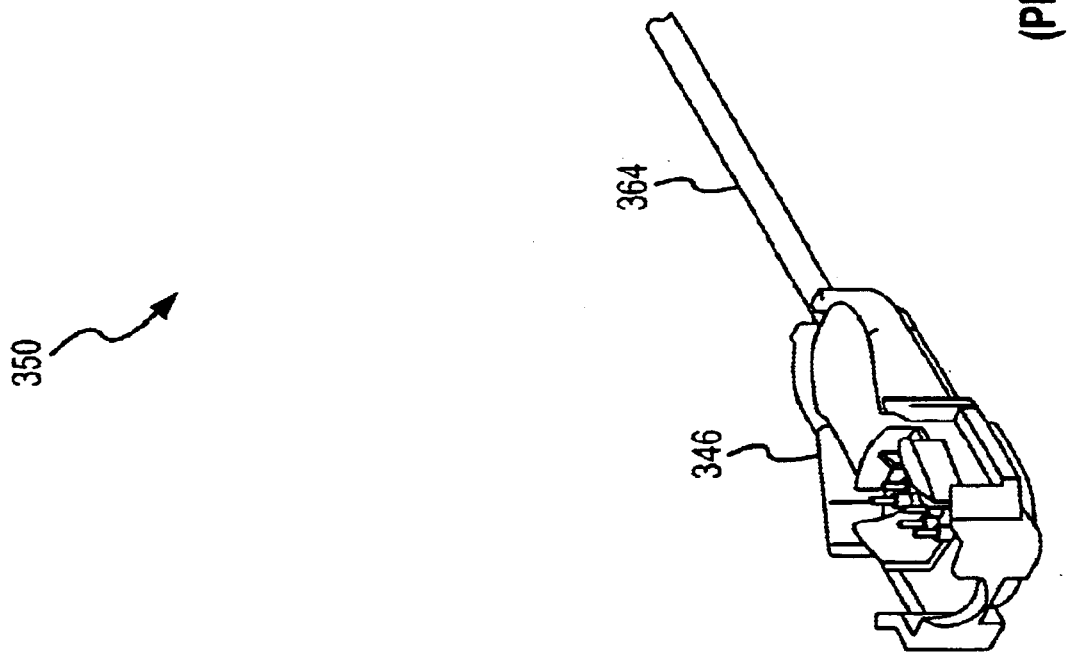

FIGS. 1–4 illustrate one embodiment of a prior art flexible oximetry sensor. FIG. 1 shows an exploded view of the sensor assembly 350. Included within the assembly 350 are upper and lower flexible members 304 and 300, respectively. These members 300, 304 are thermally bonded to one another sandwiching a leadframe 308 between their inside surfaces. This leadframe 308 contains active components (i.e., LEDs and a photodetector) for use in oximetry measurements, as will be more fully discussed in reference to FIG. 2. As will be appreciated, at least one of the flexible members 300 and 304 contains apertures 360, 362 aligned with the active components to allow a line of sight to exist between these active components and to a patient's tissue upon sensor application. The sensor assembly 350 also contains a pin connector 346 interconnected to a cable 364 that is soldered to the leadframe 308. The pin connector 346 is used to connect sensor assembly 350 to an oximetry monitor (not shown).

Figure 2:
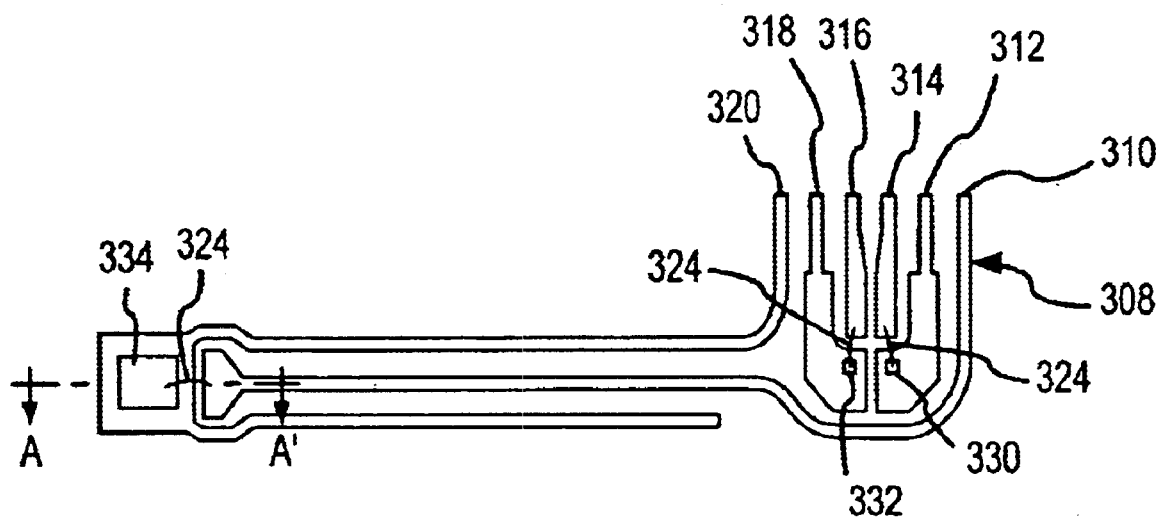
FIG. 2 shows a plan view of the metallic lead frame utilized with the pulse oximetry sensor of FIG. 1.
Figure 4:
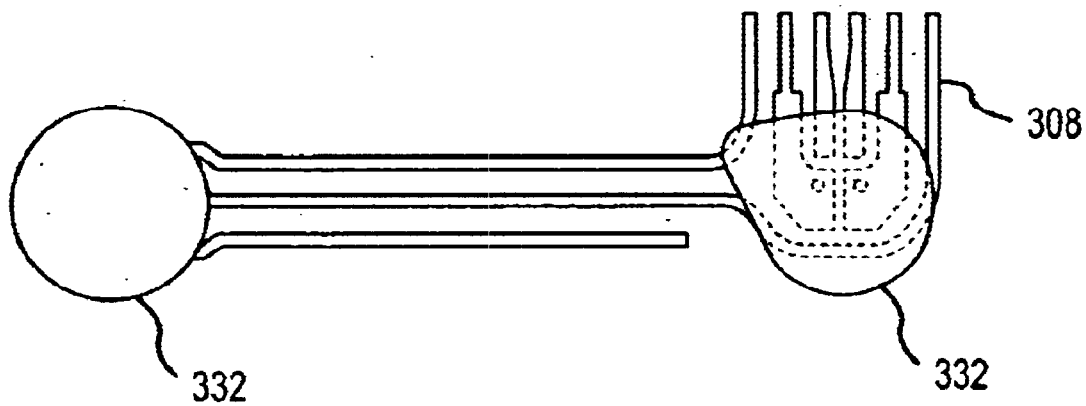
FIG. 4 shows a plan view of the metallic lead frame of FIG. 2 utilizing an adhesive encapsulant to stabilize the active components.
Figure 3:
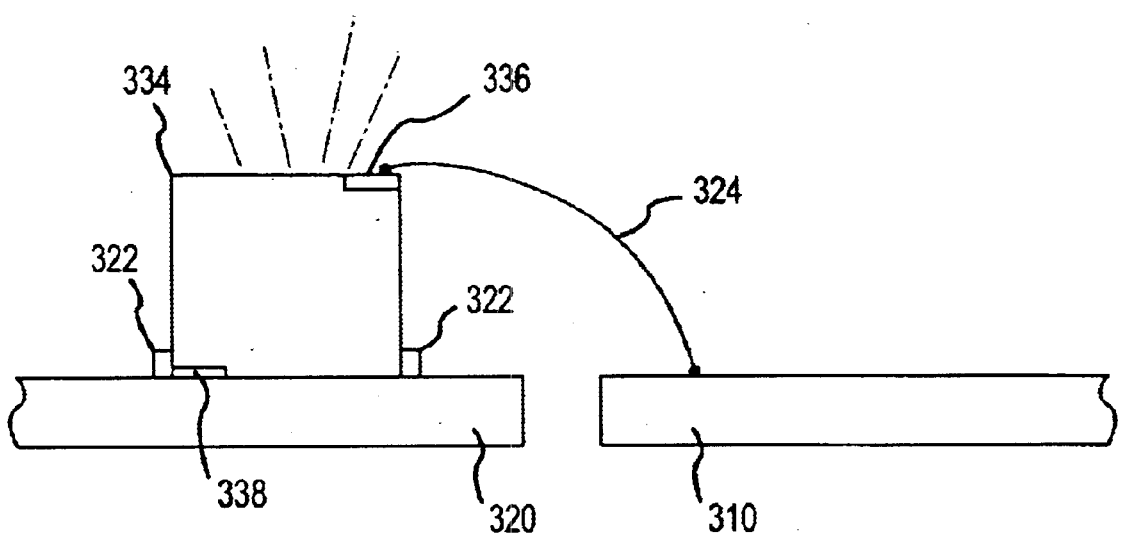
FIG. 3 shows a cross sectional view of a photodetector attached to the lead frame of FIG. 2 taken along section lines A–A'.

FIG. 2 shows a close-up view of the leadframe 308. The leadframe 308 is preferably composed of the conducting material, such as copper, and is preformed (e.g., stamp pressed or chemically etched) into a shape and size for use with the upper and lower flexible members 304 and 300. The lead frame contains a plurality of conductive traces 310–320 for conducting electrical signals through the sensor's active components 330–334. In particular the active components include LEDs 330, 332 and photodetector 334. These components 330–334 are each electrically interconnected to two of the traces to forms an electrical circuit there through. FIG. 3 shows a side view of the interconnection of the photodetector 334 to the leadframe 308 along section lines A–A'. It will be appreciated that the LED's 330 and 332 are interconnected in a substantially identical manner albeit to different electrical traces. As shown, the photodetector 334 contains first and second contact pads 336 and 338 located on its top and bottom surfaces, respectively. The bottom contact pad 338 as well as the photodetector 334 is interconnected to trace 320 by a conductive adhesive bond 322. In this regard, a drop of the conductive adhesive may be placed on the surface of the trace 320 after which the photodetector 334 is pressed into the conductive adhesive thereby creating an electrical interconnection between the bottom contact pad 338 and the trace 320. The conductive adhesive is then cured using, for example, heat. All the active components 330–334 are mounted directly to a trace 312, 318, and 320 which has a width greater than the respective component 330–330 mounted thereon. Accordingly, the emitting and detecting surfaces of the components 330–334 are necessarily mounted such that they emit/detect in a direction other than the direction of the trace on which they are mounted. As shown in FIG. 3, the photodetector's active surface is located on its top surface. Likewise, the active surfaces of the LEDs 330 and 332 are mounted to emit from their top surfaces, however, it will be appreciated that the LEDs 330, 332 also emit a substantial portion of light through their side surfaces. To complete the electrical circuit through the photodetector 334 the top contact pad 336 is interconnected to a second electrical trace 310. This connection is made using a ductile connector wire 324 (e.g., gold) that is wire bonded to the top contact pad 336, routed to the second electrical trace 310, and wire bonded to the second trace 310.

The ductile wire connector 324 is made of a small gauge wire. Additionally, the individual traces 310–320 must remain electrically isolated from one another to prevent electrical shorting there between. Therefore, in order to stabilize the wire connector 324 and isolate the traces 310–320 a clear nonconductive adhesive is utilized to encapsulate the active components 330–334 and portions of the traces 310–320. That is, a first adhesive drop 332 encapsulates the LEDs 330, 332 and a portion of all the traces 310–320 while a second adhesive drop 332 encapsulates the photodetector 334 and traces 320 and 310. These adhesive drops 332 are cured using UV light, light and/or heat to form clear solids which provide structural stability for the sensor 350 as well as lenses to help direct light emitted or received by the active components 330–334.

As will be appreciated, the prior art sensor 350 requires the forming of a conductive lead frame 308, application of active components 330–334 using a conductive adhesive, curing of the conductive adhesive, wire bonding, application and curing of clear adhesive bubbles to stabilize the sensor assembly 350, soldering the lead frame 308 to a pin connector 346 and finally sandwiching the lead frame assembly between the upper and lower flexible members 300 and 304.

Figure 5:
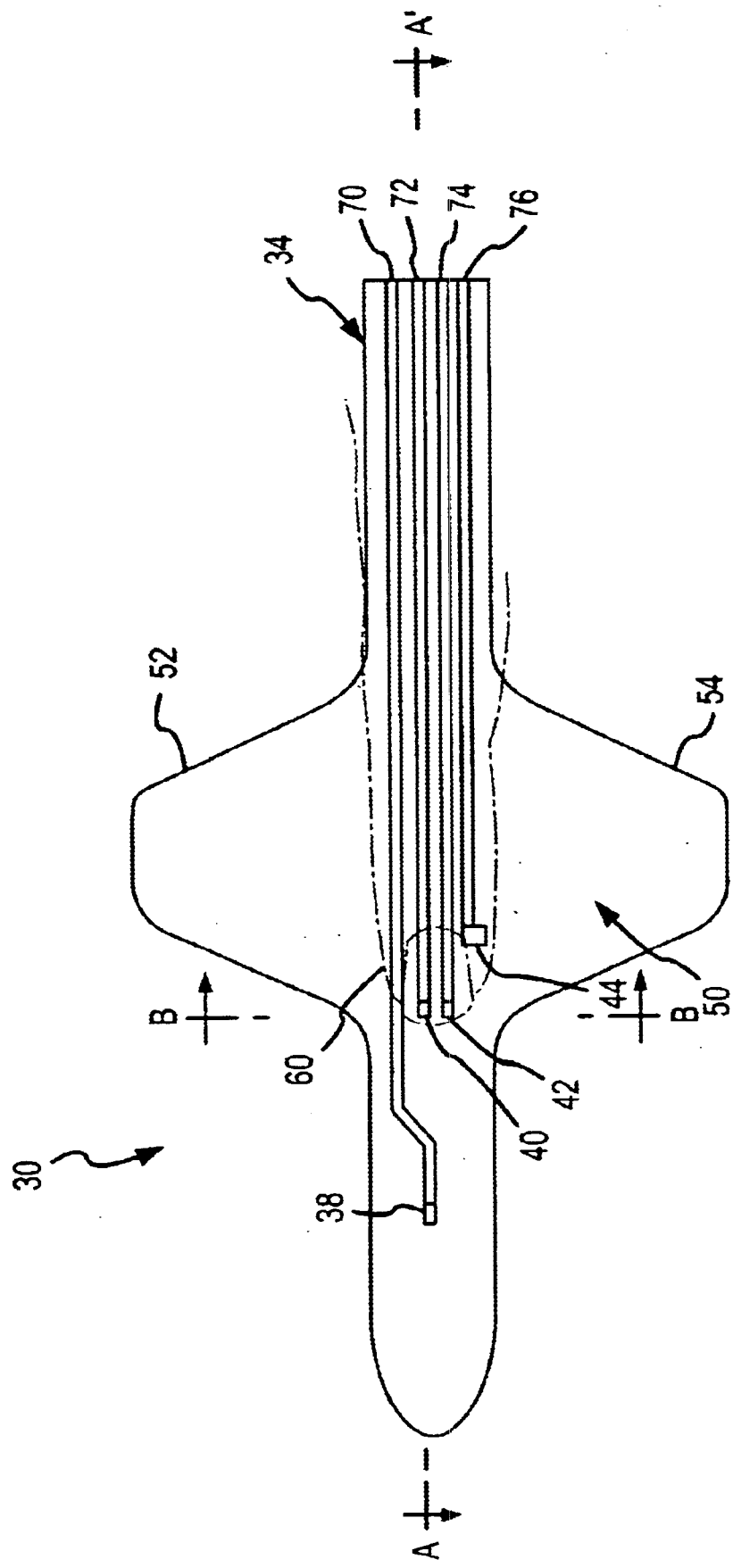
FIG. 5 shows a top plan view of a disposable sensor in accordance with the present invention.
Figure 6:
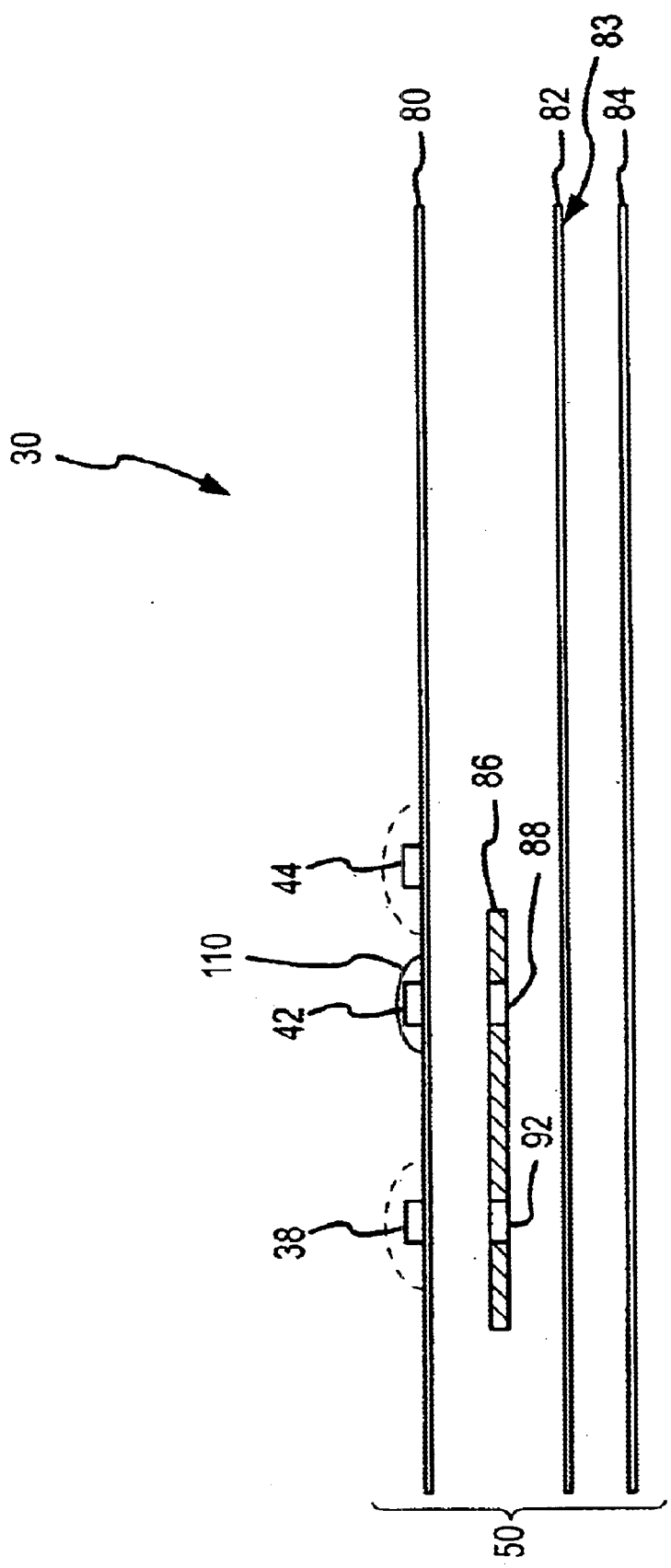
FIG. 6 shows a cross sectional view of the layers making up the disposable sensor of FIG. 5 taken along section lines A–A'.

FIG. 5 shows a top view of one embodiment of a low cost oximeter sensor assembly 30 having an integral connector 34, in accordance with the present invention. Generally, the sensor 30 is formed having a flexible sheet-like laminate 50 structure which includes first and second opposing wings 52, 54, as well as a finger-tip projection 56 oriented between and projecting perpendicular to the wings 52, 54. The wings 52, 54, along with the finger-tip projection 56, are used for flexibly wrapping the sensor 30 about a finger 60 (shown in phantom) such that one or more LED's 40, 42 are disposed on a first surface of the finger and a photodetector 38 is disposed on an opposing surface of the finger. It will be noted that the sensor 30 may be differently shaped for use with other patient extremities. The top "non-patient" side of the laminate structure 50 further contains a plurality of electrically conductive traces 70, 72, 74, 76. These traces 70, 72, 74, 76 electrically interconnect the active sensor components 38–44 to an electric power source and monitor (not shown). In particular, the sensor 30 contains a photodetector 38 interconnected to trace 70 and two light emitting diodes (LEDs) 40, 42 interconnected to traces 72 and 74, respectively. Additionally, the sensor 30 contains an identification means 44 interconnected to trace 76. This identification means 44 may be any component or combination of components. For example, the identification means 44 may comprise one or more passive and/or active electrical components (e.g., resistors, diodes, zener diodes, etc.) or memory device (e.g., a programmable integrated chip, etc.) used to provide some sort of sensor 30 identification information. IN turn, upon reading the identification means 44, an oximetry monitor (not shown) may apply appropriate calibration values related to, for example, the center wavelengths of the LEDs 40, 42 for a particular sensor 30. The active components 38–44 may be encapsulated with a clear drop 110 of adhesive (as shown in phantom lines surrounding the active components 38–44) to provide structural stability and improved optical characteristics, as will be discussed herein. FIG. 6 shows an exploded cross sectional view along projection line A–A' of the sensor 30 shown in FIG. 5. Identical components in FIGS. 5 and 6 are identified with the same reference numbers. FIG. 6 shows the different layers utilized to form the flexible substance of the present embodiment of the "laminate" sensor 30 of the present invention. Included in the laminate's layers are a clear substrate 80, an interconnecting layer 82 with a patient side adhesive surface 83 and a clear release liner 84 in face-to-face contact with the adhesive surface 83. A foam layer 86 is also disposed between a portion of the clear substrate layer 80 and the interconnecting layer 82. This foam layer 86 provides for increased patient comfort by providing cushioning and a thermal barrier between the patient's tissue and the LED's 40, 42 (LED 40 is disposed directly behind LED 42 and, therefore, not shown directly in this view), as will be more fully discussed herein. Each of the laminate's layers 80–86 are flexible such that the sensor 30 is able to conform to a patient's tissue and hold the LED's 40, 42 and the photodetector 38 relative to the tissue. Further, the interconnecting layer 82 and clear substrate 80 are made of the same/similar material, such as polyester, polyethylene, polypropylene, or polyamide so that during manufacture of the sensor 30, the clear substrate 80 and interconnecting layer 82 may be thermally bonded to one another using heat and pressure. Thermal bonding eliminates the need of a separate adhesive for attaching the clear substrate 80 and interconnecting layer 82 and also provides a method for securely holding the foam layer 86 in place (i.e., sandwiching the foam between the layers). Additionally, the heat form the thermal bonding step may be utilized to cure adhesives utilized to attach various components to the sensor 30. The foam layer 86 may be made of material similar to the clear substrate 80 and interconnecting layer 82 such that the foam layer 86 at least partially bonds to these layers 80, 82 during manufacture. The release liner 84 is made of a dissimilar material to prevent it from bonding to the interconnecting layer 82, thereby allowing it to remain removable prior to sensor application.

The release liner 84, the interconnecting layer 82, the foam layer 86 and the clear substrate layer 80 are formed of materials that are substantially transparent to ultraviolet (UV) light. This allows UV light to pass through these layers 80–86 such that any adhesives used to attach the LEDs 40, 42 and photodetector 38 to the electrical traces 70–76 and/or to the clear substrate 80 (i.e., adhesive drop 110) may be cured with light (i.e., UV or visible depending on the adhesives) applied through the bottom of the flexible substrate 50 at or near the end of the manufacturing process. The foam layer 86 contains a plurality of apertures 88–92 (Aperture 90 is aligned with LED 4 in FIG. 6 and is therefore not shown) aligned with the active components 38–44, thus allowing UV/light to access those components 38–44 for curing purposes. Further, the foam layer 86 is partially transparent, allowing a predetermined portion of light to pass through for curing and/or monitoring purposes. In the present embodiment, where there is no light blocking layer on the top side of the laminate 50, the use of substantially UV transparent materials allows for curing any adhesives with UV/light sources from either side of the sensor 30. This is especially important in other embodiments where a light blocking layer is applied to the flexible substrate 50 top surface, as will be more fully discussed herein. Alternately, thermal energy used to bond the laminate layers 50 may also be utilized to cure the adhesives used to bond the electrical components 38–44 to the sensor 50.

As noted, the clear substrate 80 is formed of a polymer thick film such as polyester, polyethylene, polypropylene, or polyamide. The clear substrate 80 provides a mounting surface for the LED's 40, 42 and photodetector 38. In this regard, these components are mounted in contact with the clear substrate 80 such that the clear substrate 80 acts at least partially as a lens, eliminating the need of separately formed lens structures for the sensor 30. However, it will be appreciated that the drops 110 of clear adhesive may also provide some focusing function for the LEDs 40, 42. That is, the adhesive drops 110 may reflect light emitted through, for example, side surfaces of the LEDs 40, 42 through the clear substrate 80.

The foam layer 86, as noted, contains three apertures 88–92, one for each of the LEDs 40, 42 and one for the photodetector 38. Accordingly, these apertures 88–92 are aligned with the LEDs 40, 42 and photodetector 38 upon assembly such that a clear line of sight exists between the LEDs 40, 42 and photodiode 38 when the sensor 30 is applied to the patient's finger 60. The LED apertures 88, 90 provide an additional benefit in that they create a trapped air pocket between the bottom surface of the clear substrate layer 80 and the interconnecting layer 82. During operation of the sensor 30, the LEDs 42, 40 produce heat which may cause the clear substrate 80 to become uncomfortably warm. Sensors utilizing copper lead frames, or copper traces formed using conventional printed board technology generally provide enough of a "heat sink" to conduct excess heat away from the LED area, preventing undue heat build up. However, in the present invention, where the traces 70–76 are formed using conductive ink, heat dissipation can become problematic. In this regard, the air pocket formed by the foam layer apertures 88, the clear substrate 80 and the interconnecting layer 82, creates a thermally insulative buffer between the patient's finger 60 and the clear substrate 80. This buffer eliminates or substantially reduces the potential for tissue damage. As will be appreciated, this air pocket may be airtight. That, is the pocket may be sealed when the clear substrate 80 and interconnecting layer 82 are thermally bonded together.

Figure 7:
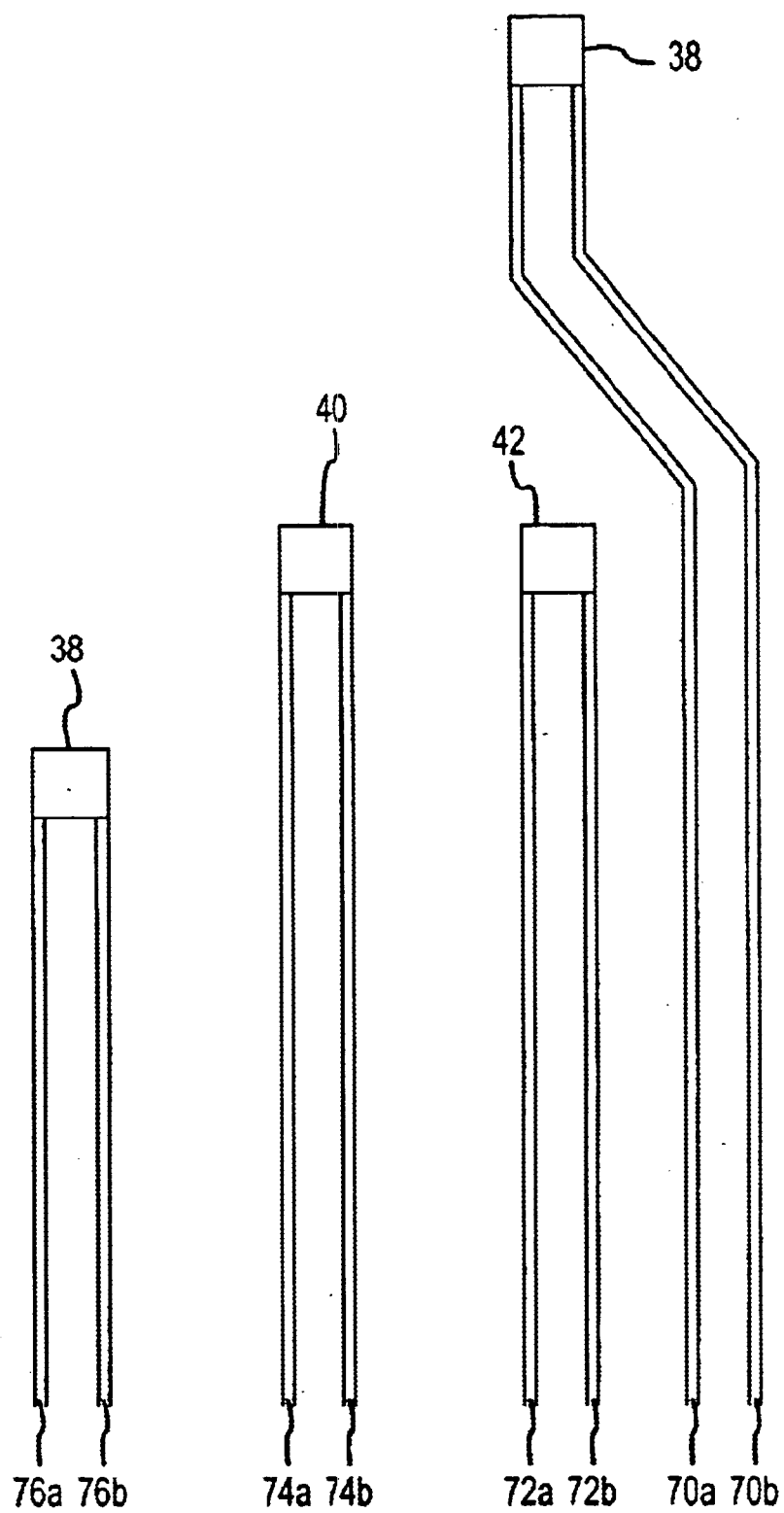
FIG. 7 shows a plan view of one embodiment of the electrically conductive traces formed on the top surface of the sensor of FIG. 5.

FIG. 7 shows a close up view of electrical traces of 70–76 and the electrical components 38, 40, 42 and 44 attached thereto. As shown, each trace 70–76 includes two substantially parallel electrically conductive paths a and b, which are electrically insulated from one another. The first half of these electrical paths (70a–76a) form "out" legs of electrical circuits and the second parallel paths (72b–76b) form the "return" legs of the electrical circuits once the sensor's active components 38–44 are interconnected to their respective traces 70–76. The traces 70–76 of the present embodiment are formed on the top surface of the clear substrate 80 using a conductive ink (e.g., epoxy with silver). This conductive ink my be deposited on the clear substrate 80 using any of a number of known ink deposition techniques such as silk screening, pad printing or inkjet printing. During the ink deposition process, the remainder of the surface of the clear substrate 80 not covered by the conductive traces 70–76 (and not to be covered by the LED 40, 42 or Photodetector 38) may also be covered by an opaque nonconductive ink. That is, the non-patient side of the clear substrate 80 may be "painted" to provide a light blocking shield for the sensor 30. Finally, any sensor identification marks may also be printed on the sensor during the ink deposition process(es). Alternatively, the traces 70–76 may include metallic conductors formed on the clear substrate using conventional printed board technology or hot foil stamping. The use of copper/metallic traces may allow for conducting heat away from the LEDs 40 during sensor operation. In addition, the metallic traces may provide for additional light reflection, providing increased signal transfer through the patient's finger 60.

Figure 8A:
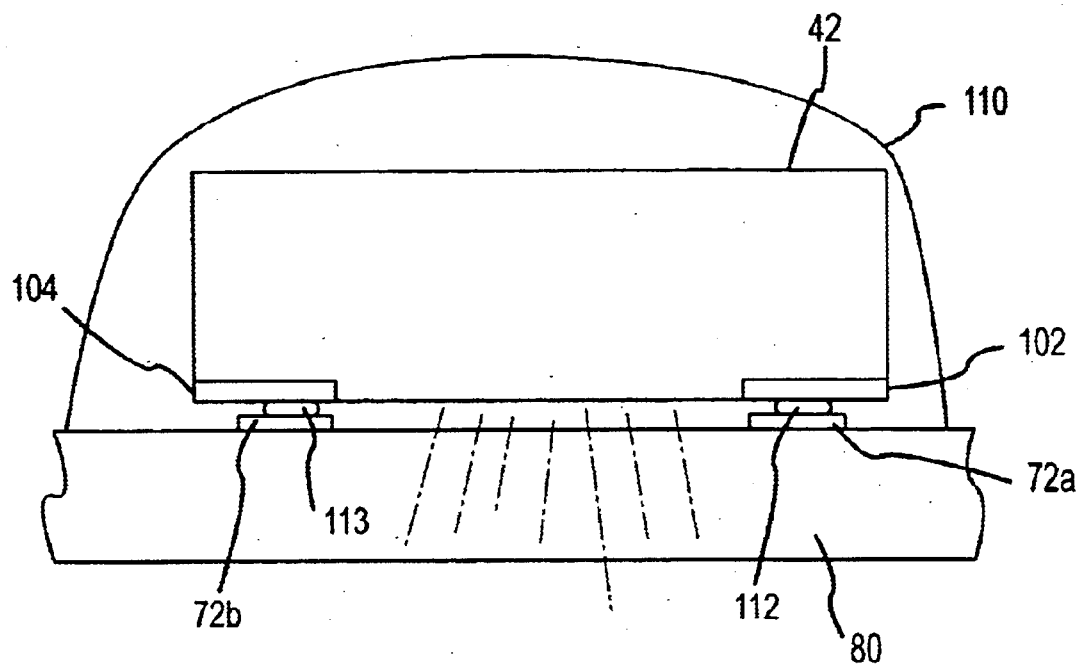
FIG. 8a shows a cross sectional view of one of the active components interconnected to the top surface of the disposable sensor of FIG. 5 taken along section lines B–B'.
Figure 8B:
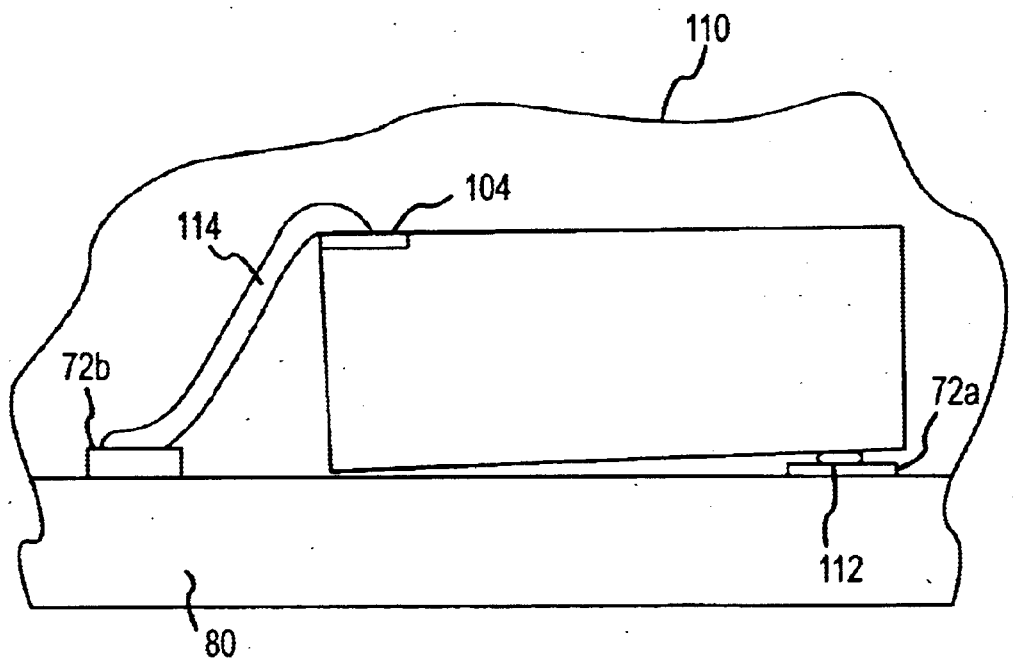
FIG. 8b shows a cross sectional view of an alternate connection one of the active components interconnected to the top surface of the disposable sensor of FIG. 5 taken along section lines B–B'.

FIGS. 8a and 8b illustrate alternate embodiments for attaching the LEDs 40, 44, photodetector 38 and identification means 44 to the traces 70–76 on the clear substrate 80. In particular, FIGS. 8a and 8b show a cross sectional view along projection line B—B' of the sensor 30 shown in FIG. 1. Though FIGS. 8a and 8b describe the attachment of LED 42 to electrical trace 72, it is to be understood that any or all of the active components 33–44 of the sensor 30 contain similar structures and may be interconnected to their respective traces 70–76 in a substantially identical manner. As shown in both FIGS. 8a and 8b, LED 42 contains a first electrical contact pad 102 and a second electrical contact pad 104. These electrical contact pads 102, 104 are interconnectable with the out leg 72a and return leg 72b of electrical trace 72. In accordance with the present invention, the LED 42 is mounted such that it emits light through the clear substrate 80 which, in turn, acts as a lens for the LED 42.

In FIG. 8a, LED 42 is shown as a "flip chip" having both electrical contact pads 102, 104 located on the same surface of the LED 42. Further, the first and second electrical contact pads 102, 104 are located on the same surface as the LED's light emitting surface. In this regard, the electrical contact pads 102, 104 are easily interconnected to the out and return legs 72a and 72b on the clear substrate 80 using an electrically conductive adhesive to form conductive bonds 112, 113 between the trace legs 72a, 72b and the contact pads 102, 104.

FIG. 8b illustrates an alternative embodiment for use when LED 42 contains first and second electrical contact pads 102, 104 oriented on opposing faces of the LED 42. In this arrangement, a bead of the conductive adhesive is used to interconnect the top electrical contact pad 104 to the return leg 72b of the trace 72. That is, the electrically conductive adhesive is used to create an electrical conduit 114. The bottom contact pad 102 is again directly interconnected to the out leg 72a of the electrical trace 72 using a conductive bond 112. As will be appreciated, in both embodiments using the electrically conductive adhesive eliminates the need for wire bonding and/or soldering of the LED 42 to the trace 72. The conductive bonds 112, 113 and/or 114 may then cured (i.e. thermally or with light).

In addition to being attached to the clear substrate via the electrically conductive bonds 112, 113 and/or 114, a clear adhesive is used to attach LED 42 to the clear substrate 82. The clear adhesive creates an adhesive drop 110 that encapsulates the entire LED 42 and the electrical connections to the electrical traces. Upon curing, the adhesive drop 110 provides stability for the electrical connections and also increases light focusing through the clear substrate 80 by refracting light emanating through the sides of the LED 42 through the clear substrate 80. As will be appreciated, the LED 42 must attached to the electrical out and return legs (72a and 72b) of the electrical trace 72 with the conductive adhesive 112 prior to encapsulating the LED 42. The clear adhesive may then be applied around and flowed into any spaces beneath the LED 42 to secure the LED 42 to the clear substrate 80. Preferably, the clear adhesive covers the entire LED 42, thereby encapsulating the LED 42 within the drop 110. The clear adhesive may then be cured thermally or by utilizing light that may be applied from above or beneath the sensor laminate 50 as described above. If the conductive adhesive is viscous enough to maintain the bond between the contact pads 102 and 104 and traces 72a and 72b during encapsulation, curing of the conductive and clear adhesives may be done simultaneously.

Figure 9:
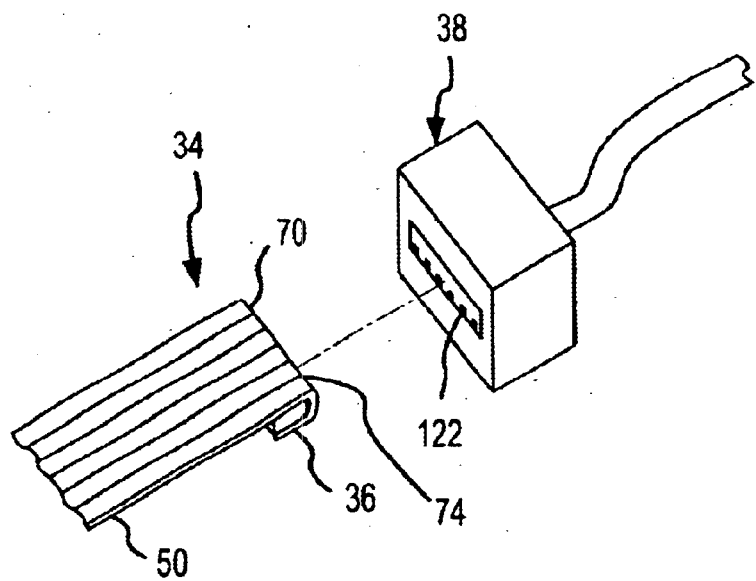
FIG. 9 shows a perspective view of one embodiment the integral connector of the disposable sensor of FIG. 5.
Figure 10:
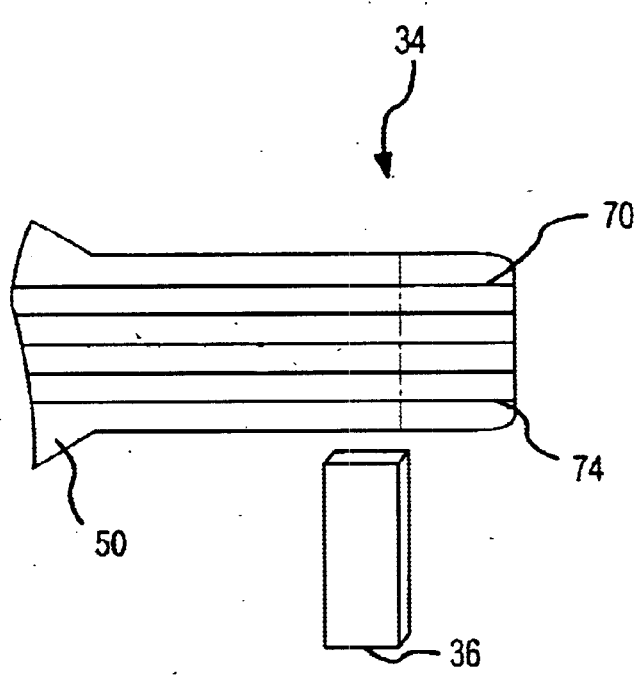
FIG. 10 shows a stiffener utilized with the integral connector of FIG. 9.

FIGS. 9 and 10 illustrate various components of the integral connector 34 formed on one end of the sensor 30. The integral connector 34 is designed to interface to the connector plug 38 which is interconnected with an oximetry monitor (not shown). Generally, the connector plug 38 contains an opening 120 having a plurality of contact pins 122 which are operable to interconnect with the traces 70–74 located on the clear substrate 80. The contact pins 122 act as springs such that upon insertion of the integral connector 34 within the connector plug opening 120 the contact pins 120 maintain contact pressure with the traces 70–76. As will be appreciated, a contact pin exists for each out leg and each return leg of each of the traces 70–76. As shown in FIG. 10, the integral connector 34 is formed by folding the laminate 50 along a fold line 64 such that the traces 70–76 on the non-patient surface of the clear substrate are exposed on both sides of the integral connector 34. In order to provide the structural integrity necessary for the connector 34 to interface with the connector plug 38, a stiffener 36 is inserted in the fold of the laminate structure 50. This stiffener 36 may be made of any suitable material that has a relative stiffness greater than that of the flexible substrate 50. Preferably, the stiffener 66 will be made of a similar material to the flexible substrate 50 rest of the sensor 30 such that it may be thermally bonded in place. The stiffener 36 provides structural stiffness, allowing a technician to interconnect the integral connector 34 with the connector plug 38. Additionally, the stiffener 36 provides volume within the fold such that the connector pins 122 within the connector plug 38 may effectively contact with the traces 70–76 upon insertion.

Figure 11:
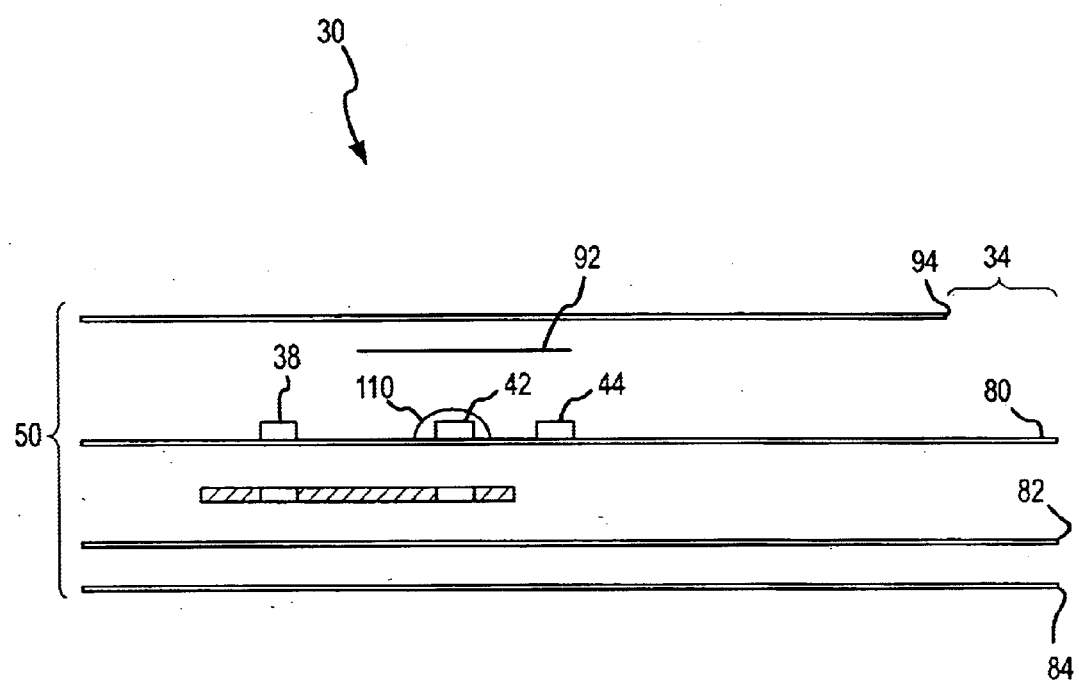
FIG. 11 shows a cross sectional view of an alternate combination of layers making up the disposable sensor of FIG. 5 taken along section lines A–A', wherein said sensor includes a thermal element.
Figure 12:
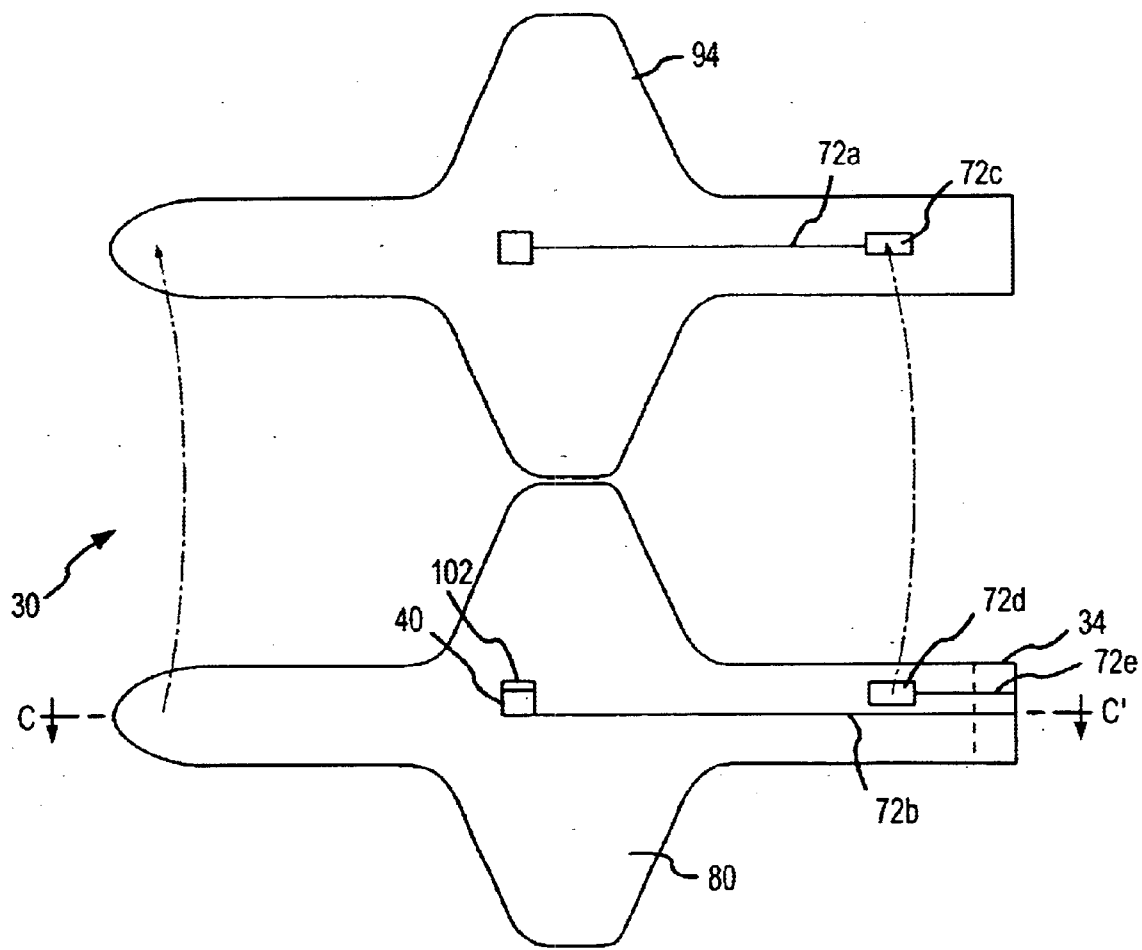
FIG. 12 shows a plan view of a flexible sensor in accordance with the present invention that utilizes two flexible substrates having electrically conductive traces formed thereon.

FIGS. 11 and 12 illustrate another embodiment of the sensor in accordance with the present invention. This second embodiment is similar in structure to the first embodiment shown in FIGS. 5 and 6, however, this embodiment further utilizes a cover layer 94 covering the top surface of the clear substrate. FIG. 11 shows a plan view of the top surface of the clear substrate 80 and the bottom surface of the cover layer 94. FIG. 12 shows an exploded side view along projection line C–C' of FIG. 11 and includes the cover layer 94. The cover layer 94 covers substantially the entire top surface of the clear substrate 80, excluding the portion of the clear substrate that makes up the integral connector 34. The cover film layer 94 is generally an opaque flexile layer made of a material similar to the clear substrate 80 and is utilized for its light blocking characteristics. As with the embodiment of FIGS. 5 and 6, the cover layer 94 may be thermally bonded to the clear substrate 80 during manufacture. In addition, the embodiment shown in FIGS. 11 and 12 includes a heat sink 92 that is disposed between the clear substrate 80 and the cover layer 94 in the region of the LEDs 40, 42. Upon sensor assembly, the heat sink 92 is "sandwiched" between the cover layer 94 and the clear substrate 80. The heat sink may be any thermally conductive material, such as a copper disk, that provides adequate heat transfer away from the LEDs 40, 42 to prevent the LEDs 40, 42 from overheating during sensor operation. This heat sink 92 is especially desirable when conductive inks are utilized to form the traces 70–76, as conductive inks generally do not provide enough thermal mass to provide adequate heat transfer away from the LEDs 40, 42, which can lead to patient discomfort and/or tissue damage (i.e. burns).

In the embodiment of FIGS. 11 and 12 the cover layer 94 contains one or more of the traces 70–76 utilized for connecting the active components 38, 42, 40, 44 of the sensor 30. FIG. 12 shows a plan view of the bottom of the cover layer 94 and the top of the clear substrate 80 prior to lamination (not to scale). For clarity herein only LED 40 and the electrical traces connected thereto are described. In particular, the LED 40 contains a contact pad 104 interconnected to the clear substrate layer 80 (See FIG. 8b) and a contact pad 102 on its top surface. Accordingly, the cover layer 94 contains one of the out or return legs (i.e., a or b) of electrical trace 72 to facilitate electrical connection. As noted for simplicity, only one electrical component (LED 40) and its corresponding trace 72 are illustrated, however it is to be understood all the traces 70–76 for all active components are formed in a like manner. In this embodiment, the LED's bottom contact pad 104 (not shown) is electrically interconnected with trace 72b located on the clear substrate 80 using, for example, a conductive adhesive. The LED's top contact pad 102 is interconnected to trace 72a located on the bottom surface of the cover layer 94. As will be appreciated, upon lamination of the sensor 30 the cover layer trace 72a is electrically isolated from the corresponding clear substrate layer traces 72b. That is, each trace leg a and b is offset or jogged such that they take an individual path to and from the LED 40. Finally, to utilize the integral connector 34 in accordance with the present invention, both legs a and b of the conductive traces 72 must be disposed on the outside of the clear substrate 80 when folded. Accordingly, the cover layer 94 does not extend to the sensor's integral connector 34 section (see FIG. 12). To provide electrical connections to the cover layer trace 74a, the cover layer trace 74a further contains a contact pad 74c that is able to electrically mate with a contact pad 74d on the clear substrate 80 when the cover layer 94 and clear substrate 80 are contacted. The clear substrate contact pad 72d further contains an electrical trace 74e that leads to the integral connector 34. Upon sensor lamination, the contact pads 74c, 74d are thermally and electrically bonded and provide electrical connection to the integral connector 34.

The cover layer 94 provides for added sensor structural integrity and additional protection for the electrical components 38–44. As will be appreciated, when the cover layer 94 is utilized, all the electrical components 38–44 are sandwiched between the cover layer 94 and clear substrate 80. As these layers are thermally bonded in the lamination of the sensor 30, the resulting laminate 50 has its active components 38–44 securely embedded within, providing a sensor assembly having increased resiliency.

Figure 13:
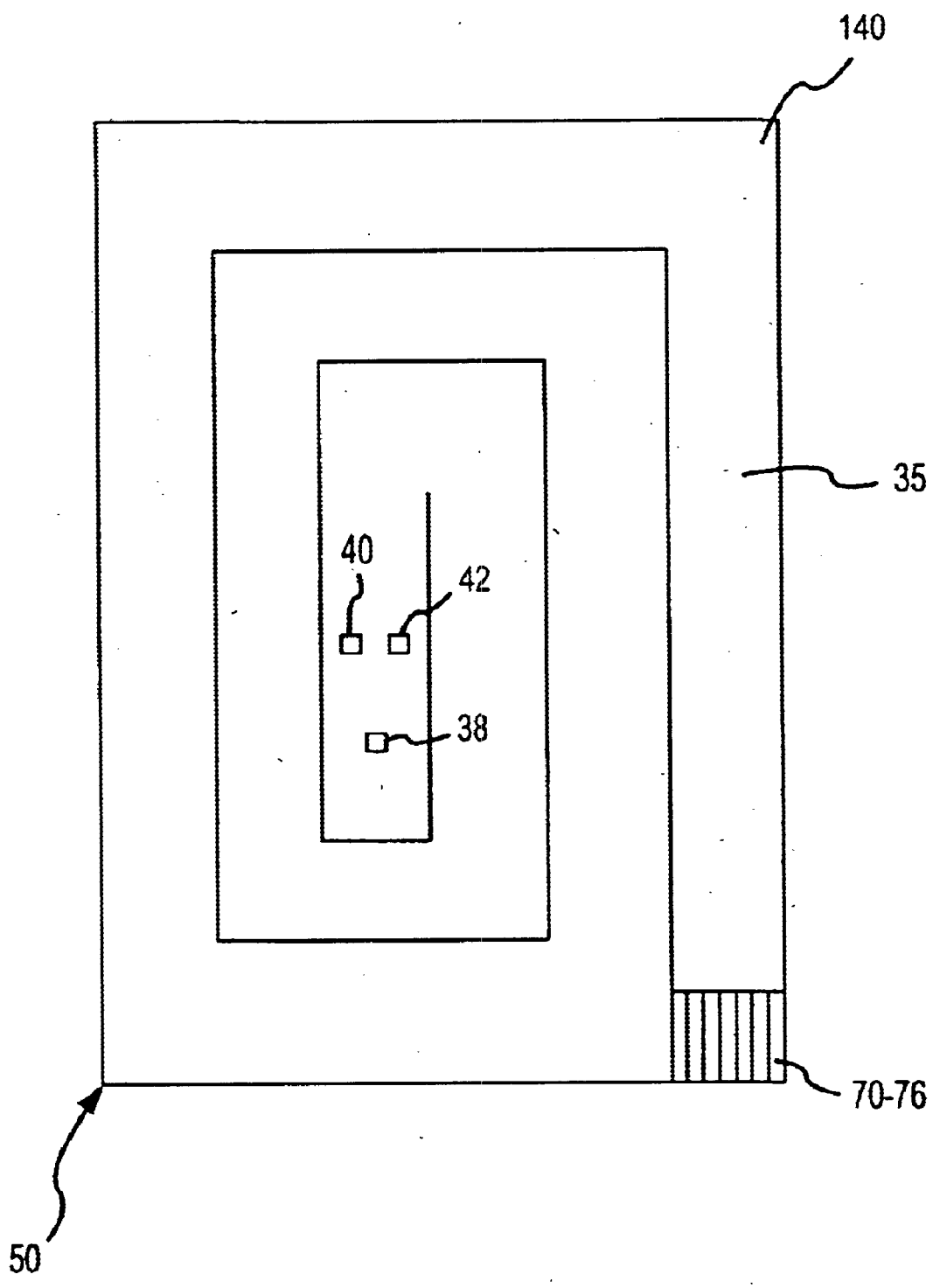
FIG. 13 shows a plan view of a flexible sensor of the present invention having an integrally formed cord.
Figure 14A:
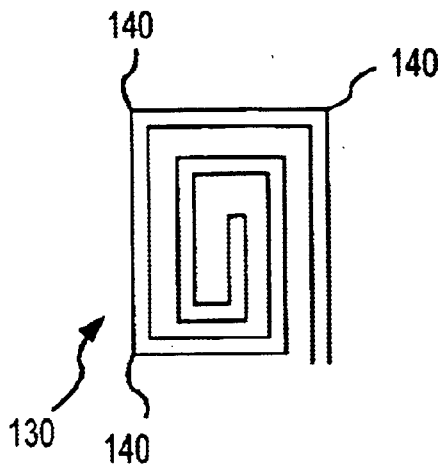
FIGS. 14a–d shows a process for straightening the cord of the flexible sensor of FIG. 13.
Figure 14B:
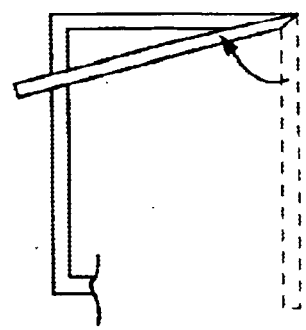
Figure 14C:
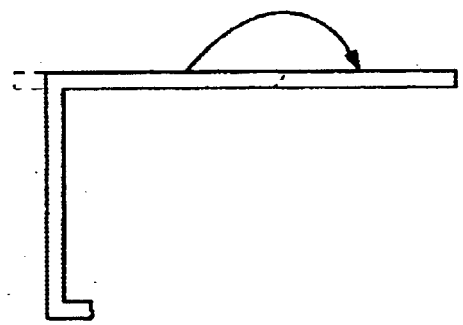
Figure 14D:
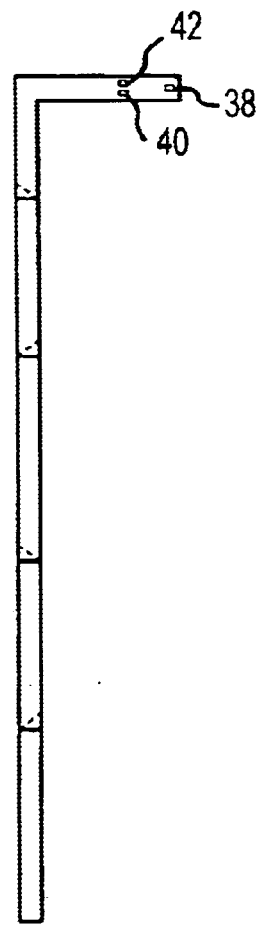

FIG. 13 shows another embodiment of the present invention. In this embodiment, the clear structure 80 and the conductive traces 70–76 are formed in a square concentric spiral pattern on a single sheet of laminate. The concentric sensor 130 contains LEDs 40, 42 a photodetector 38 and an identification means 44 all located at the end of the concentric traces 70–76 near the middle of the sheet of laminate. In accordance with the present invention, the LED's 40, 42 and the photodetector 38 may be mounted such that they emit/detect through a clear substrate. The concentric sensor 130 may utilize any combination of layers as described in relation to the embodiments above. What is important is that the concentric sensor provides a sensor having an integrally formed cable that is formed on a single "sheet" of laminate while producing an integral cable that is longer than the outside dimensions of the sheet. In this regard, after the traces are applied to the laminate sheet, the sheet is cut between the concentric traces 70–76 to produce a integral cable 35 that has a square spiral shape (see FIG. 14a). In order to straighten the cable, the square corners 140 of the sensor 130 are each first folded back at a 45 degree angle (See FIG. 14b) and then refolded straight forward (see FIG. 14c), allowing the integral cable 35 to take the form of a long strip (FIG. 14d). As will be appreciated, the integral cable allows the connection of the sensor 130 to a monitor to be made at an increased distance away from the patient's tissue.

Figure 15:
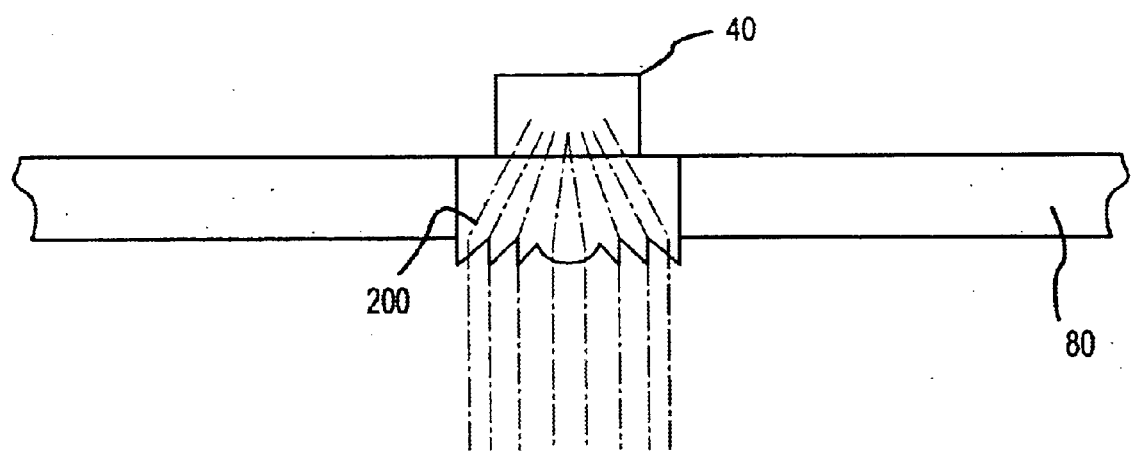
FIG. 15 shows a fresnel lens that may be incorporated into the clear substrate of any of the above embodiments of the sensor.

As will be appreciated, any of the previous embodiments may further utilize additional layers/materials to provide further enhanced sensor characteristics. For example, as shown in FIG. 15, a separate lens structure may be utilized if the refractive properties of the clear substrate 80 are not sufficient to properly direct/focus the light emitted/received by the emitters/detector 40, 42 and/or 38.14 In this regard, a lens, such as a fresnel lens 200, may be integrally formed into the clear substrate 80. Alternatively the clear substrate 80 may be over-molded onto an existing lens 200. In either case, an LED 40 may be mounted upon the back surface of the lens 200 to allow the light emitting from the LED 40 to be concentrated into a more unidirectional light beam.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A flexible pulse oximetry sensor, said sensor comprising:
   a substantially clear flexible substrate having first and second surfaces;
   at least one of:
      a light emitter mounted on said first surface of said clear substrate for emitting light through said substrate and said second surface; and
      a light detector mounted on said first surface of said clear substrate for detecting light through said second surface and said substrate and providing a signal indicative of said detected light; and
   a substantially clear adhesive for at least partially attaching by way of direct interconnection said at least one of said light emitter and said light detector to said clear substrate.

2. The pulse oximetry sensor of claim 1, further comprising:
   a substantially clear adhesive on said second surface for securing said sensor to a patient's tissue.

3. The pulse oximetry sensor of claim 2, further comprising:
   a substantially clear release liner for covering said adhesive, wherein said release liner may be selectively removed prior to application of said sensor to a patient's tissue.

4. The pulse oximetry sensor of claim 1, wherein said clear adhesive encapsulates said at least one of said light emitter and said light detector.

5. The pulse oximetry sensor of claim 1, wherein said clear adhesive is light curable.

6. The pulse oximetry sensor of claim 1, further comprising:
   a substantially clear interconnecting layer interconnected to at least a portion of said second surface of said clear substrate;
   an at least partially transparent compressible layer disposed between at least a portion of said interconnecting layer and said clear substrate; and
   a substantially clear adhesive on at least a portion of said second surface for securing said sensor to a patient's tissue.

7. The pulse oximetry sensor of claim 6, wherein said compressible layer has a transparency index of at least 0.4.

8. The pulse oximetry sensor of claim 6, wherein said compressible layer contains at least a first aperture for each said light emitter and said light detector, wherein each said aperture is aligned with each said light emitter and light detector to allow light to pass through said aperture free from interference.

9. The pulse oximetry sensor of claim 8, wherein said interconnecting layer, said aperture and said clear substrate form an air pocket.

10. The pulse oximetry sensor of claim 9, wherein said air pocket is air tight.

11. The pulse oximetry sensor of claim 1, wherein said sensor contains at least one light emitter, further comprising:
   a thermal element being adapted to transfer thermal energy away from said at least one light emitter.

12. The pulse oximetry sensor of claim 1, wherein said clear flexible substrate further comprises a lens integrally formed within said substrate to focus light relative to said at least one of light emitter and light detector.

13. The pulse oximetry sensor of claim 1, wherein said substantially clear flexible substrate at least partially forms a connector adapted to connect said pulse oximetry sensor to a monitor.

14. A flexible pulse oximetry sensor, said sensor comprising:
   a substantially clear flexible substrate having a first surface with at least one electrically conductive trace formed thereon; and
   at least one of:
      a light emitter mounted on said first surface of said clear substrate and electrically interconnected to at least one said trace, said light emitter for emitting light through said substrate and a second surface of said substrate; and
      a light detector mounted on said first surface of said clear substrate and electrically interconnected to at least one said trace, said light detector for detecting light through said second surface and said substrate and providing a signal indicative of said detected light.

15. The pulse oximetry sensor of claim 14, further comprising:
   a substantially clear adhesive on said second surface for securing said sensor to a patient's tissue.

16. The pulse oximetry sensor of claim 15, wherein said at least one electrically conductive trace is formed from a conductive ink deposited onto said clear substrate.

17. The pulse oximetry sensor of claim 16, wherein said conductive ink is deposited on said first surface using a printing process.

18. The pulse oximetry sensor of claim 15, wherein said at least one electrically conductive trace is formed from a metallic foil stamped onto said clear substrate.

19. The pulse oximetry sensor of claim 14, wherein said substantially clear flexible substrate at least partially forms a connector adapted to connect said pulse oximetry sensor to a monitor.

20. A flexible pulse oximetry sensor, said sensor comprising:
   a substantially clear flexible substrate having at least one electrically conductive trace formed on a first surface;
   at least a first light emitter electrically interconnected to at least one said electrically conductive trace on said flexible substrate, said light emitter for emitting light through said substrate relative to a patient's tissue; and
   a thermal element being adapted to transfer thermal energy away from said at least one light emitter when said light emitter is emitting light; and
   an adhesive on said second surface of said flexible substrate for securing said sensor to a patient's tissue.

21. The pulse oximetry sensor of claim 20, wherein said at least one electrically conductive trace is formed from a conductive ink printed on said flexible substrate.

22. The pulse oximetry sensor of claim 20, wherein said thermal element comprises a thermally conductive material at least partially covering said first surface.

23. The pulse oximetry sensor of claim 22, wherein said thermally conductive material is electrically isolated from said at least one electrically conductive trace.

24. The pulse oximetry sensor of claim 20, wherein said substantially clear flexible substrate at least partially forms a connector adapted to connect said pulse oximetry sensor to a monitor.

25. A flexible pulse oximetry sensor, said sensor comprising:
   a substantially clear flexible substrate having first and second surfaces; and
   at least one of:
      a light emitter mounted on said first surface of said clear substrate for emitting light through said substrate and said second surface; and
      a light detector mounted on said first surface of said clear substrate for detecting light through said second surface and said substrate and providing a signal indicative of said detected light; and
   an insulative layer in a face to face relationship with at least a portion of said second surface for creating a temperature differential between a patient's tissue and said second surface opposite said at least one emitter and detector.

26. The pulse oximetry sensor of claim 25, further comprising:
   a substantially clear interconnecting layer interconnected to at least a portion of said insulative layer; and
   an adhesive on the bottom surface of said interconnecting layer for attaching said sensor to a patient's tissue.

27. The pulse oximetry sensor of claim 26, wherein said insulative layer contains at least a first aperture for each said light emitter and each said light detector, wherein said aperture is aligned with said light emitter and said light detector to allow light to pass through said aperture free from interference.

28. The pulse oximetry sensor of claim 27, wherein said clear substrate second surface, said aperture and said interconnecting layer are adapted to create an air pocket between said substrate and a patient's tissue.

29. The pulse oximetry sensor of claim 28, wherein said air pocket is substantially sealed.

30. The pulse oximetry sensor of claim 25, wherein said substantially clear flexible substrate at least partially forms a connector adapted to connect said pulse oximetry sensor to a monitor.

31. A flexible pulse oximetry sensor, said sensor comprising:
   a first flexible substrate having a first surface with at least a first electrically conductive trace thereon,
   a second flexible substrate having a first surface having at least a first electrically conductive trace thereon, wherein said first substrate first surface and second substrate first surface are in a face to face relationship and wherein one of said substrates is substantially clear,
   at least one of:
      a light emitter mounted on the first surface of one of said first and second substrates, wherein said light emitter is electrically interconnected to at least one trace on said first substrate and at least one trace on said second substrate and wherein said light emitter emits light through said substantially clear substrate; and
      a light detector mounted on the first surface of one of said first and second substrates, wherein said light detector is electrically interconnected to at least one trace on said first substrate and at least one trace on said second substrate and wherein said light detector detects light though said substantially clear substrate; and
   an adhesive on a second surface of one of said first and second substrates for securing said sensor to a patient's tissue.

32. The sensor of claim 31, wherein said first substrate traces and second substrate traces are electrically isolated.

33. The sensor of claim 31, wherein at least one of said light emitter and light detector is mounted to said clear substrate allowing light to be one of emitted through said clear substrate and detected through said clear substrate.

34. The sensor of claim 31, wherein the other of said first and second substrates is substantially opaque.

* * * * *